United States Patent
Croisard et al.

(10) Patent No.: US 9,586,206 B2
(45) Date of Patent: Mar. 7, 2017

(54) REACTION VESSEL FOR AN AUTOMATIC CHEMICAL OR BIOLOGICAL ANALYSIS APPLIANCE

(75) Inventors: Philippe Croisard, Acheres (FR); Olivier Valverde, Levallois (FR)

(73) Assignee: DIAGNOSTICA STAGO, Asnieres-sur-Seine (FR)

(*) Notice: Subject to any disclaimer, the term of this patent is extended or adjusted under 35 U.S.C. 154(b) by 721 days.

(21) Appl. No.: 13/876,030

(22) PCT Filed: Oct. 4, 2011

(86) PCT No.: PCT/FR2011/052310
§ 371 (c)(1),
(2), (4) Date: Mar. 26, 2013

(87) PCT Pub. No.: WO2012/045972
PCT Pub. Date: Apr. 12, 2012

(65) Prior Publication Data
US 2013/0183213 A1    Jul. 18, 2013

(30) Foreign Application Priority Data

Oct. 5, 2010 (FR) .................................. 10 58041
May 31, 2011 (FR) .................................. 11 54790

(51) Int. Cl.
*A61J 1/06* (2006.01)
*B01L 3/00* (2006.01)
(Continued)

(52) U.S. Cl.
CPC .......... *B01L 3/508* (2013.01); *B01L 3/50855* (2013.01); *G01N 33/4905* (2013.01);
(Continued)

(58) Field of Classification Search
CPC ........ B01L 3/50; B01L 3/5025; B01L 3/5082; B01L 2200/028; G01N 35/00; G01N 35/02; G01N 35/026
(Continued)

(56) References Cited

U.S. PATENT DOCUMENTS 3,194,426 A * 7/1965 Brown, Jr. .................. 220/23.4
3,521,785 A * 7/1970 Soelter et al. ............... 220/23.4
(Continued)

FOREIGN PATENT DOCUMENTS

EP    0 325 874    8/1989
EP    1 792 656    6/2007
(Continued)

OTHER PUBLICATIONS

International Search Report dated Dec. 9, 2011, corresponding to PCT/FR2011/052310.

*Primary Examiner* — Jill Warden
*Assistant Examiner* — Dwayne K Handy
(74) *Attorney, Agent, or Firm* — Young & Thompson

(57) ABSTRACT

A reaction vessel for an automatic chemical or biological analysis appliance includes a connection part (22) for connection to another vessel (10) of the same type, the connection part is resiliently snap-fastened on the top end of the vessel (10) and is also resiliently snap-fastened to the connection part (22) of another vessel so as to form a string of vessels that are hinged to one another about transverse axes (xx)'.

3 Claims, 6 Drawing Sheets

(51) Int. Cl.
*G01N 33/49* (2006.01)
*G01N 35/04* (2006.01)

(52) U.S. Cl.
CPC ...... *G01N 35/04* (2013.01); *B01L 2300/0809* (2013.01); *Y10T 29/49826* (2015.01)

(58) Field of Classification Search
USPC ........................................ 422/547, 549, 554
See application file for complete search history.

(56) References Cited

U.S. PATENT DOCUMENTS

| | | | |
|---|---|---|---|
| 4,918,984 A | | 4/1990 | Martinoli et al. |
| 4,944,924 A | * | 7/1990 | Mawhirt et al. ............... 422/562 |
| 5,019,243 A | * | 5/1991 | McEwen et al. ................ 210/94 |
| 5,651,941 A | * | 7/1997 | Stark et al. .................... 422/562 |
| 6,241,949 B1 | * | 6/2001 | Kane ..................... B01L 3/5085 |
| | | | 422/553 |
| 6,291,249 B1 | * | 9/2001 | Mahant et al. ............... 436/177 |
| 7,824,615 B2 | * | 11/2010 | Balli ............................... 422/65 |
| 7,943,100 B2 | | 5/2011 | Rousseau |
| 7,959,878 B2 | | 6/2011 | Rousseau |

FOREIGN PATENT DOCUMENTS

| | | |
|---|---|---|
| FR | 2 873 447 | 1/2006 |
| FR | 2 896 589 | 7/2007 |
| FR | 2 917 828 | 12/2008 |
| WO | 03/065047 | 8/2003 |
| WO | 2007/039524 | 4/2007 |

\* cited by examiner

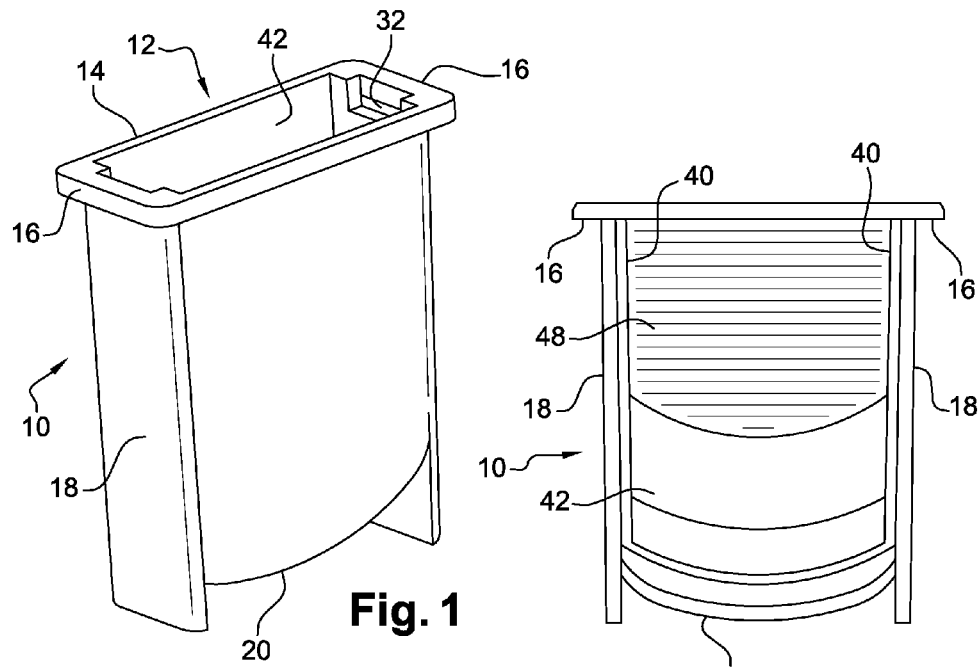
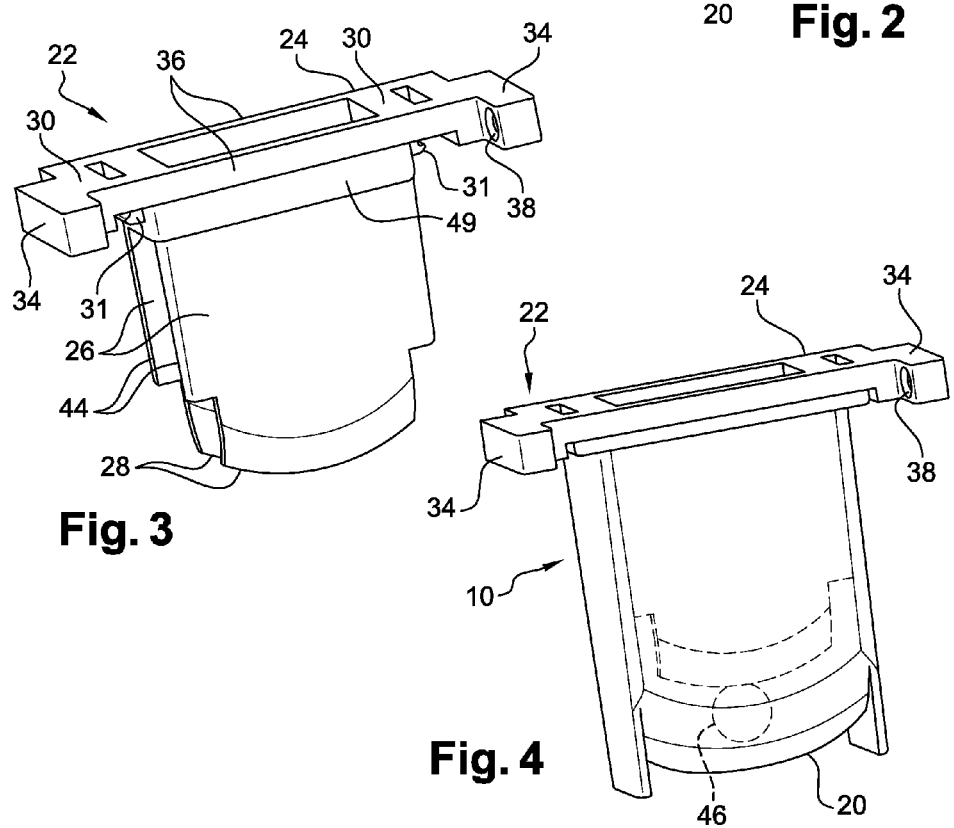

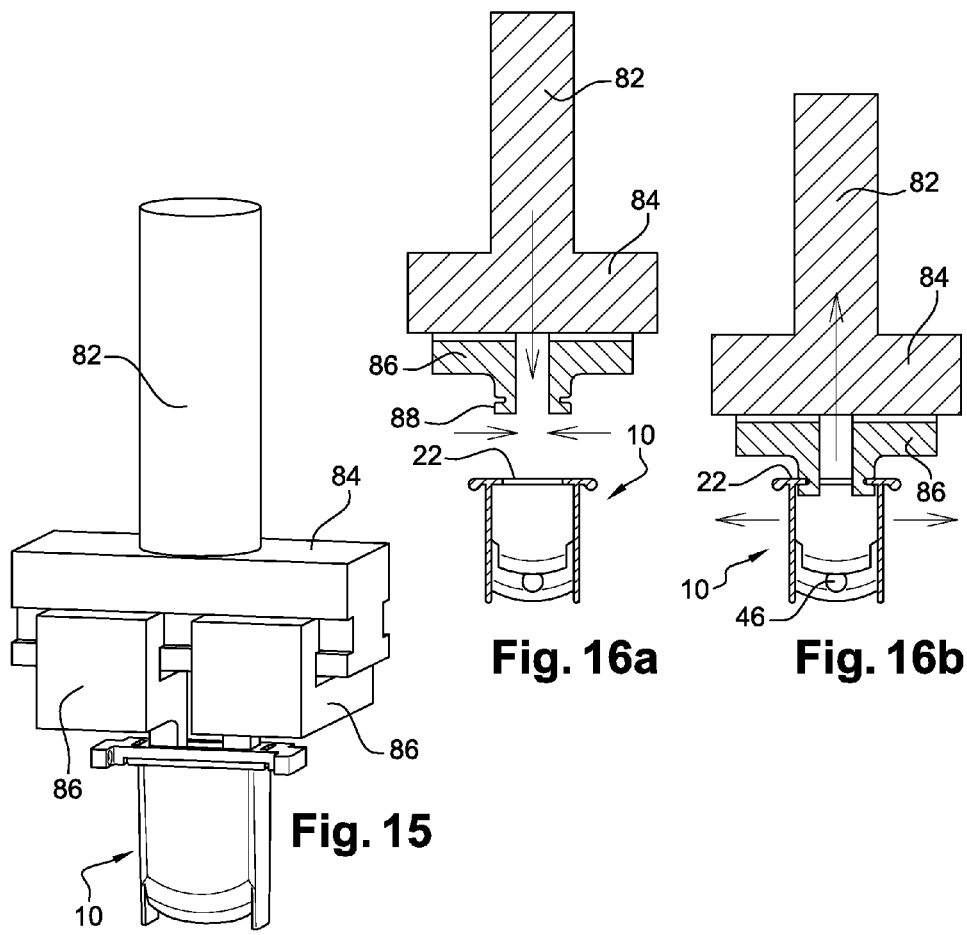
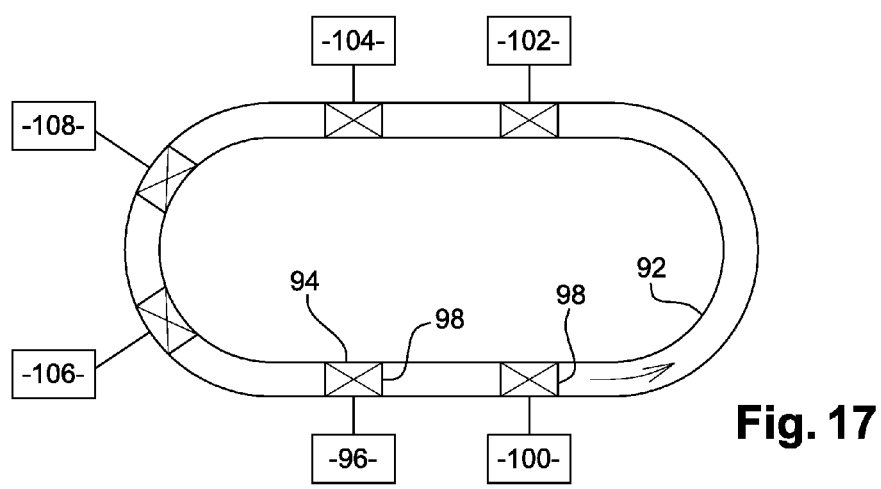

REACTION VESSEL FOR AN AUTOMATIC CHEMICAL OR BIOLOGICAL ANALYSIS APPLIANCE

The invention relates to a reaction vessel for an automatic chemical or biological analysis appliance, to a set of such vessels, and to an assembly made up of a vessel and a gripper device.

Documents EP-A-0 325 874 and WO-A-03/065047 disclose vessels of this type that are used for example to determine the time required for the physical state of a medium to change, in particular for determining the coagulation time of a sample of blood, such a vessel being open at its top end and having a curved bottom forming a rolling path for a bead of ferromagnetic material that is movable in the vessel in periodic manner by means of an external magnetic field, the variations in the amplitude and/or the frequency of the movements of the bead being representative of the physical state of the blood sample.

In document WO-A-03/065047, the vessels containing beads are fastened side by side in detachable manner on a flexible support film that closes their top ends and that is suitable for being wound on a reel in order to feed an automatic analysis appliance and cause the vessels to travel in succession through the appliance.

The film has slots or orifices in register with the openings in the vessels so that samples and reagents can be deposited in the vessels, while also serving to retain the beads in the vessels.

At their top ends, the vessels have two lateral rims or lugs formed with projecting spikes for being engaged by force in lateral perforations in the film, the rims of the vessels fastened to the film forming a rack enabling the assembly comprising the film together with the vessels to be moved by meshing with a cog belt or the like.

Those known means present numerous advantages, but also a few drawbacks: the vessels need to be fastened to the film and then detached therefrom after utilization, which operations cannot be performed perfectly so there is a risk of a vessel becoming detached either prematurely or late. They also present a cost that is not negligible compared with the cost of the vessels, which cost needs to be added to the cost of the film onto which the vessels are fastened.

While the vessels or the reels having films carrying vessels wound thereon are being moved, it can happen that the beads contained in the vessels are not properly held by the film carrying the vessels and that they escape therefrom. Under such circumstances, the intended analyses cannot be performed correctly in the vessels and need to be done again, resulting in losses of samples, of reagents, and of time.

Furthermore, loading the vessels on a reel in the analysis appliance does not make it possible to have a buffer stock of vessels in the appliance while the reel is being loaded, thereby requiring the appliance to be stopped while loading is taking place. Separating the film from the vessels can also give rise to breakage of the spikes or of the lateral rims of the vessels, and also to beads escaping, which can lead to the appliance becoming blocked or to the vessel-loading device becoming blocked.

A particular object of the present invention is to avoid those drawbacks of the prior art in a manner that is simple, effective, and inexpensive.

To this end, the invention provides a reaction vessel for an automatic chemical or biological analysis appliance, the vessel having an open top end and containing fluid stirring means, the vessel being characterized in that its top end carries a connection part for attaching to an identical connection part of another vessel of the same type, the connection part being fastened on the top end of the vessel by resilient snap- or clip-fastening.

Thus, in the invention, the vessels are connected together by connection parts, each of which is carried by the top end of a vessel and is attached to the connection part of another vessel. Connecting the vessels together in this way avoids the drawbacks associated with the prior art use of the plastics film and thus makes it possible to eliminate the spikes provided on the lateral rims of the vessels in the prior art.

Advantageously, the connection part includes attachment and hinging means for attaching to the connection part of another vessel and for hinging about a transverse axis parallel to an edge of the top end of the vessel.

Thus, the interconnected vessels form a hinged sequence, thereby making the vessels easier to store and stow, and also making them easier to load and move through the automatic analysis appliance.

According to another advantageous characteristic of the invention, the attachment means of the connection part are means for resilient snap- or clip-fastening.

By means of this characteristic, the connection parts can be mounted on the vessels and attached to one another without it being necessary to use any tool.

According to another characteristic of the invention, the connection part fastened to the top end of the vessel includes retaining means for retaining the fluid stirring means, the retaining means extending inside the vessel.

When the means for stirring the fluid contained in the vessel comprise a bead of ferromagnetic material, the retaining means formed on the connection part comprise at least a thin plate extending downwards inside the vessel along a longitudinal wall thereof and presenting a bottom edge forming an edge for guiding and retaining the above-mentioned bead.

Preferably, the connection part comprises two of the above-mentioned thin plates that are parallel and that extend downwards along two opposite longitudinal walls of the vessel and that have bottom edges forming two parallel edges for guiding and retaining the ferromagnetic bead in the vessel.

The vertical edges of the or each thin plate may be guided between the longitudinal wall of the vessel and vertical splines may be formed to project from the inside faces of the transverse walls of the vessel.

In a variant embodiment of the invention, the connection part includes a tongue closing the open top end of the vessel, at least in part, in such a manner as to retain the fluid stirring means in the vessel.

In preferred manner, the tongue is elastic and can be folded towards the inside of the vessel in order to give easier access to the inside volume of the vessel and in order to make it easier, for example, to deposit a sample or a reagent.

In another variant embodiment, the connection part includes a tongue extending outwards for the purpose of closing, at least in part, the open top end of an adjacent vessel to which said vessel is attached, so as to retain the fluid stirring means in the adjacent vessel.

In this way, once the vessels are attached to one another, the tongue of one vessel prevents the stirring means of an adjacent vessel from escaping accidentally.

In a preferred embodiment of the invention, the connection part comprises a rectangular frame fitted on the open top end of the vessel and carrying attachment means for attaching to a connection part of another vessel.

The rectangular frame of the connection part has two parallel arms extending outwards in line with its short sides, the ends of these two arms including attachment means for attaching to complementary means formed on the rectangular frame of a connection part of another vessel.

The rectangular frame of the connection part also includes means for resilient snap- or clip-fastening on the top end of the vessel.

Advantageously, the above-mentioned connection part is made of substantially opaque plastics material.

Thus, the content of the reaction vessel is protected against being illuminated by an external light source, which under certain circumstances can facilitate or improve reading the result of a reaction.

The invention also provides a set of reaction vessels for an automatic chemical or biological analysis appliance, the set being characterized in that it comprises a plurality of reaction vessels of the above-described type, which vessels are connected to one another in a continuous string by the connection parts and are spiral-wound on a circular support for loading into the analysis appliance or are arranged in parallel rows in a vertical or horizontal loader.

The invention also provides an assembly comprising at least one reaction vessel and a gripper device for gripping said reaction vessel, the assembly being characterized in that the gripper device comprises a cylindrical rod that is movable vertically and that carries attachment means for attaching to the rectangular frame of the connection part, these attachment means being movable in horizontal translation on the cylindrical rod.

Finally, the invention provides a method of assembling reaction vessels of the above-described type, the method being characterized in that it comprises the steps consisting in:

placing vessels on supports having locations for receiving and positioning vessels, these locations being arranged to form strings of vessels that are spaced apart from one another at a predetermined pitch;

placing stirring means, e.g. such as a ferromagnetic bead, in each of the vessels positioned on the above-mentioned supports;

placing connection parts on the vessels positioned on the above-mentioned supports, and resiliently snap-fastening them thereto;

using video inspection to verify that stirring means are present in the vessels and that the connection parts are snap-fastened on the vessels; and moving the vessel supports through various stations designed to perform the above-specified steps.

This device for assembling vessels is much simpler and more reliable than the prior art device for assembling them to a plastics film.

The invention can be better understood and other characteristics, details, and advantages thereof appear more clearly on reading the following description made by way of example with reference to the accompanying drawings, in which:

FIGS. 1 and 2 are diagrammatic perspective and section views of a reaction vessel of the invention;

FIG. 3 is a diagrammatic perspective view of a connection part;

FIG. 4 is a diagrammatic perspective view showing a vessel fitted with a connection part;

FIG. 15 is a diagrammatic perspective view of a gripper device for gripping a vessel of the invention;

FIGS. 16a and 16b are diagrams showing the operation of the FIG. 15 gripper device; and FIG. 17 is a diagram of a device for assembling vessels of the invention.

Figure 5:
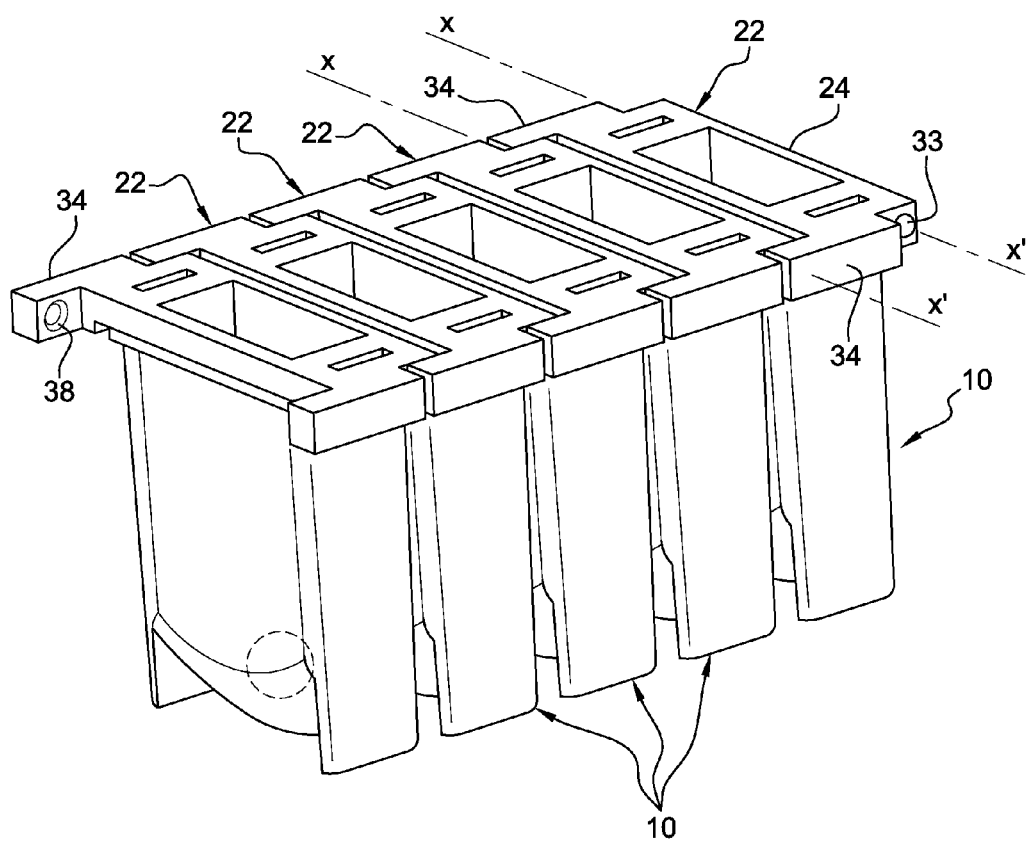
FIG. 5 is a diagrammatic perspective view showing a plurality of vessels connected together by connection parts.

Reference is made initially to FIGS. 1 to 4 which show a first embodiment of the invention in which the reaction vessel 10 made of transparent plastics material is generally in the form of a rectangular parallelepiped with an open top end 12 surrounded by a frame 14 having two side rims or lugs 16 connected to the lateral short sides 18 of the vessel and perpendicular to said lateral short sides.

The bottom 20 of the vessel is curved with its concave side facing upwards and it forms a guide path for fluid stirring means constituted by a bead of ferromagnetic material such as the bead 46 shown in FIG. 4.

This reaction vessel 10 typically has a height of 15 millimeters (mm) and a cross-section of 10 mm×4 mm, with a working volume of 490 cubic millimeters ($mm^3$) (420 $mm^3$ when the vessel is provided with the connection part).

It is associated with a connection part 22 shown in FIG. 3, which part is made of preferably opaque plastics material and essentially comprises at its top end a rectangular frame 24, and two thin plates or jaws 26 that are vertical and parallel, being connected at their top ends to the long sides of the frame 24, these two jaws 26 being identical and mirror images of each other.

Their bottom ends 28 are curved both in a longitudinal plane and in a transverse plane so as to correspond to the curvature of the curved bottom 20 of the vessel 10, the two bottom ends 28 of the jaws 26 forming edges for guiding and retaining the bead 46 of ferromagnetic material placed in the vessel 10 on its curved bottom. These ends 28 are spaced apart from each other by a distance that is less than the diameter of the bead.

The rectangular frame 24 is of dimensions substantially equal to or slightly greater than the dimensions of the frame 14 of the vessel 10 and it is pressed against the frame 14 when the connection part 22 is mounted inside the vessel 10, as shown diagrammatically in FIG. 4.

On their bottom faces, the short sides 30 of the frame 24 include rims 31 for attaching in windows 32 at the top ends of the short walls of the vessel by resilient snap- or clip-fastening, with the ends of the rims 31 engaging under the rims or lugs 16 of the frame 14 of the vessel. The outer vertical faces of these short sides of the frame also include respective projecting hemispheres 33 (see FIG. 5), the two hemispheres 33 being in alignment parallel to a long side of the frame 24 and forming a portion of the means for attaching the connection part 22 to another, identical connection part that is associated with another vessel 10.

The frame 24 also has two parallel branches 34 formed at the ends of a long side 36 of the frame 24, the branches 34 extending perpendicularly to the long side 36 and being spaced apart from each other by a distance equal to the length of the other long side of the frame 24. The inner vertical face of each branch 34 includes a hemispherical cavity 38 for receiving a hemispherical projection 33 of another connection part 22 when two vessels 10 are to be connected together, as shown in FIG. 5, the two hemispherical cavities 38 of the branches 34 being in alignment with each other, parallel to the long side 36 of the frame 24.

Furthermore, means are provided so that the jaws 26 of the part 22 remain parallel when the connection part 22 is mounted on the vessel 10, in order to enable the bottom ends 28 of the jaws 26 to perform properly their role of guiding and retaining the ferromagnetic bead 46 resting on the curved bottom 20 of the vessel. By way of example, these means are constituted by vertical splines 40 projecting from the inside faces of the side walls 18 of the vessel, the splines 40 co-operating with the vertical long walls 42 of the vessel to define slideways for guiding the vertical edges 44 of the jaws 26 of the part 22.

As shown diagrammatically in FIG. 2, the inside face of each long wall 42 of the vessel is "frosted", i.e. it is not smooth but presents a certain amount of roughness, at least in its upper portion 48, so as to limit the amount of liquid that rises by capillarity in the narrow gap formed between this wall and the corresponding jaw 26 of the connection part. Furthermore, a horizontal strip 49 is formed as an extra thickness on the outer face of each jaw 26 at its top end, this strip 49 being pressed against the inner face of the wall 42 of the vessel when the part 22 is mounted on the vessel, and acting as a seal or gasket closing the gap between the jaw 26 and the wall 42 of the vessel.

In order to assemble the vessels to one another, a connection part 22 is presented above each vessel 10 containing a ferromagnetic bead 46 and it is lowered into the vessel until the frame 24 of the part 22 rests on the frame 14 of the vessel and is fastened to the frame by resilient snap- or clip-fastening. In this position, the bottom ends 28 of the jaws 26 of the part 22 are situated immediately above the bead of ferromagnetic material resting on the curved bottom 20 of the vessel and they prevent the bead from escaping from the vessel. It then suffices to attach the vessels to one another by engaging the branches 34 of one connection part 22 of one vessel on the short sides 30 of the frame 24 of another connection part 22 fastened to another vessel, mutual attachment of the two connection parts 22 taking place by resilient snap- or clip-fastening as a result of the branches 34 being deformed outwards a little while they are being engaged on the hemispherical projections 32 of the other connection part. It is thus possible to attach a series of vessels 10 to one another in order to form a string as shown in FIG. 5, the vessels being hinged to one another about transverse axes xx' formed by the projections 33 housed in the cavities 38.

In the string of vessels as constituted in this way, the branches 34 of the connection part 22 form projections for meshing with teeth of a drive member in an automatic analysis appliance.

Figure 6:
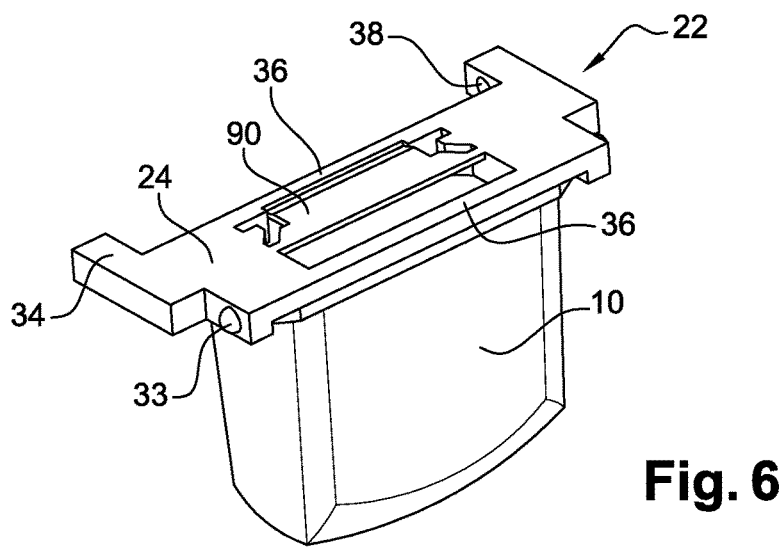
FIG. 6 is a diagrammatic perspective view of a vessel fitted with a connection part in a variant embodiment of the invention.
Figure 7:
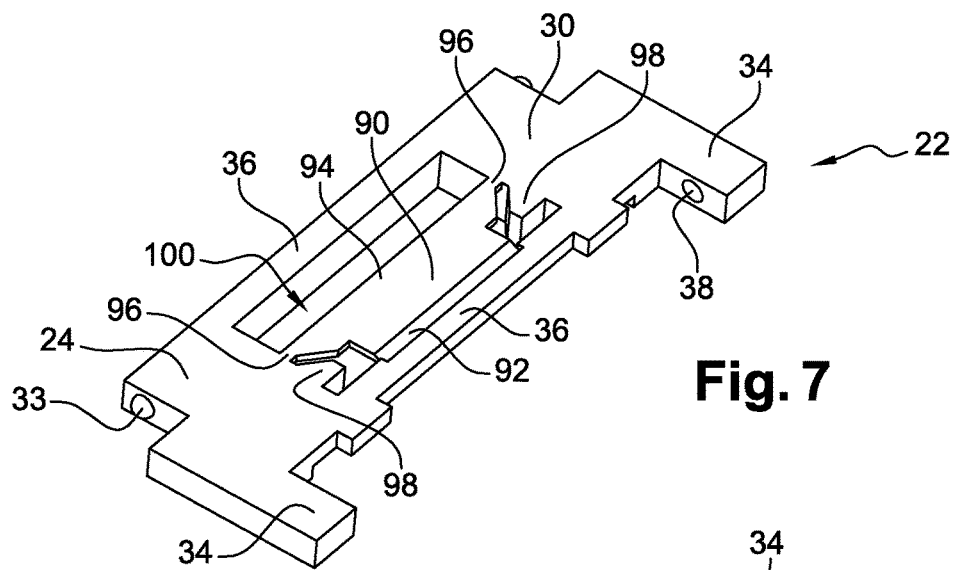
FIGS. 7 and 8 are diagrammatic perspective views respectively from above and from below of the FIG. 6 connection part.
Figure 8:
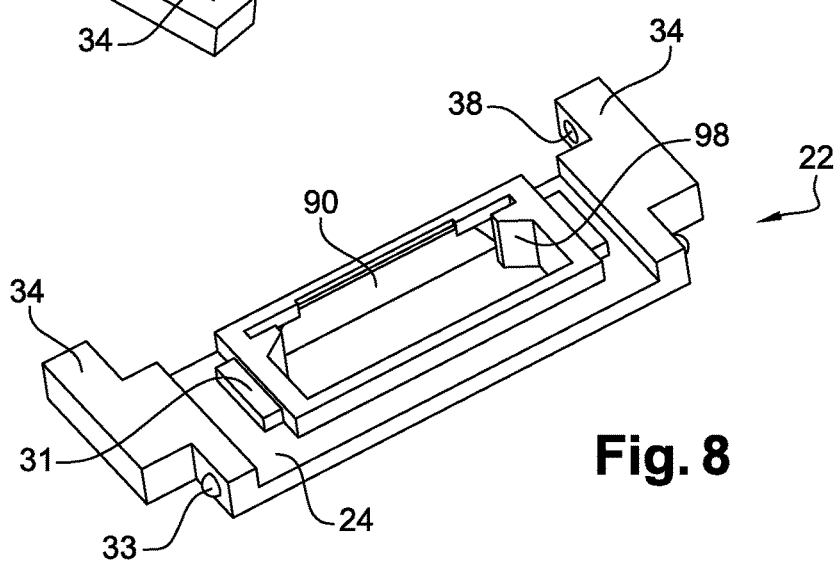

FIGS. 6 to 8 show a variant of the invention in which the connection part 22 does not have vertical jaws 26. The bead 46 is held inside the vessel 10 by a tongue or flap 90 closing the open top end 12 of the vessel 10, at least in part, so as to retain the bead 46 in the vessel 10.

This flap 90 is integrally molded with the frame 24 and is generally trapezoidal in shape. The flap 90 has a short longitudinal edge 92 connected to one of the long sides 36 of the frame 24 and a long longitudinal edge 94 having two ends 96 that are releasably connected respectively to the short sides 30 of the frame 24 (FIG. 7).

After cutting through the connection zones between the above-mentioned ends 96 of the flap 90 and the frame 24, e.g. by pressing on the flap 90, the flap can be pivoted about its short longitudinal edge 92 between a shut position shown in FIGS. 6 and 7, in which it extends in the plane of the frame 24 and at least partially closes the opening in the frame 24 and the vessel 10, and an access position in which it is folded downwards so as to give easier access to the inside volume of the vessel 10, e.g. for the purpose of placing a sample or a reagent therein.

Each short side 30 of the frame 24 also includes a snap-fastener stud 98 projecting into the opening of the frame 24 towards the opposite short side 30. The studs 98 hold the flap 90 in the access position.

In the example shown in FIGS. 6 to 8, the flap 90 does not close the opening in the frame 24 completely, a slot 100 of width less than the diameter of the bead 46 being left between the flap 90 and the opposite long side 36 of the frame 24. In this way, in the shut position, the bead 46 cannot be extracted from the vessel 10.

Figure 9:
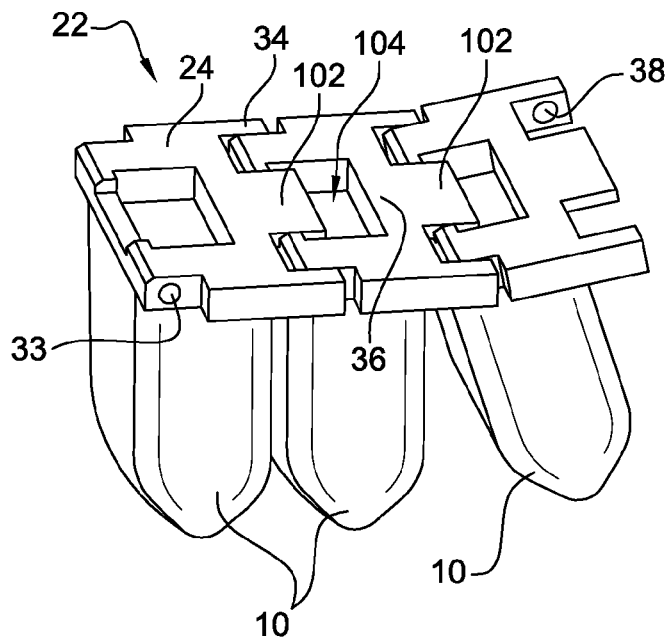
FIG. 9 is a diagrammatic perspective view showing a plurality of vessels attached to one another by connection parts, in another variant embodiment of the invention.
Figure 10:
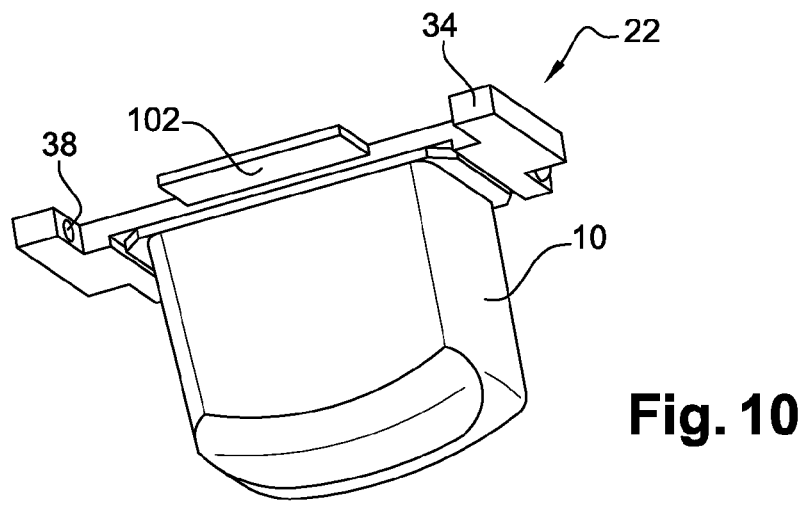
FIG. 10 is a perspective view from above of a vessel and a connection part in the variant of FIG. 9.
Figure 11:
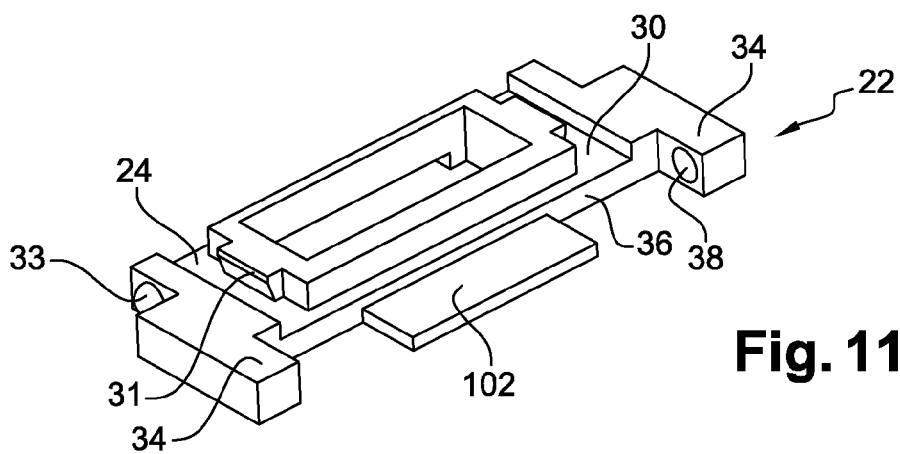
FIG. 11 is a perspective view from below of the FIG. 10 connection part.

FIGS. 9 to 11 show another variant in which the connection part 22 likewise does not have vertical jaws 26, and the bead 46 is held inside the vessel 10 by a tongue 102 of an adjacent connection part 22.

Each connection part 22 has a tongue 102 extending outwards from the long side 36 of the frame 24 that has the branches 34 attached thereto. The tongue 102 lies in the plane of the frame 24, its length being determined in such a manner that said tongue 102 closes, at least in part, the open top end 12 of an adjacent vessel to which said vessel is attached, so as to retain the bead 46 in the adjacent vessel.

In the example shown in FIGS. 9 to 11, the tongue 102 does not completely close the opening 12 of the adjacent vessel 10, with a slot 104 (FIG. 9) of width smaller than the diameter of the bead 46 being left between the free end of the tongue 102 and the opposite long side 36 of the corresponding frame 24. In this way, the bead 46 cannot be extracted from the adjacent vessel 10.

The connection parts 22 of FIGS. 6 to 11 remain similar to the part described above with reference to FIGS. 1 to 5 in that they likewise include branches 34 and attachment means 33, 38 for co-operating with complementary attachment means of a connection part 22 of another vessel 10. These vessels 10 can thus be attached to one another so as to form a string of vessels 10.

Figure 12:
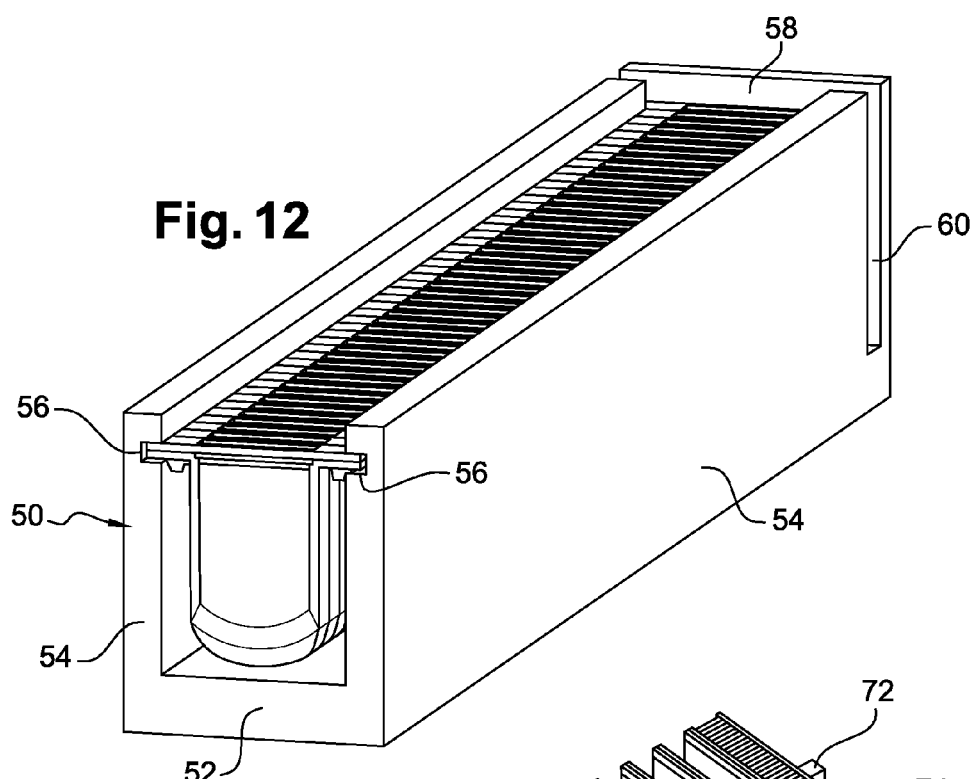
FIG. 12 is a diagrammatic perspective view of a storage drawer for vessels of the invention.

The strings of reaction vessels can be stored in drawers 50 such as that shown in FIG. 12, the drawer having a bottom wall 52 and two parallel side walls 54 that are connected together by the bottom wall 52, these two side walls 54 including, in the vicinity of their top ends, respective horizontal grooves 56 forming slideways for guiding and holding the branches 34 of the connection parts 22.

One end of the drawer 50 is closed by a transverse wall 58 perpendicular to the side walls 54, the other end of the drawer being opened so as to allow reaction vessels to be inserted and extracted.

In the vicinity of the wall 58, a slot 60 may optionally be provided in the walls 54 in order to pass a pusher enabling the reaction vessels to be pushed towards the opposite open end of the drawer 50.

Figure 13:
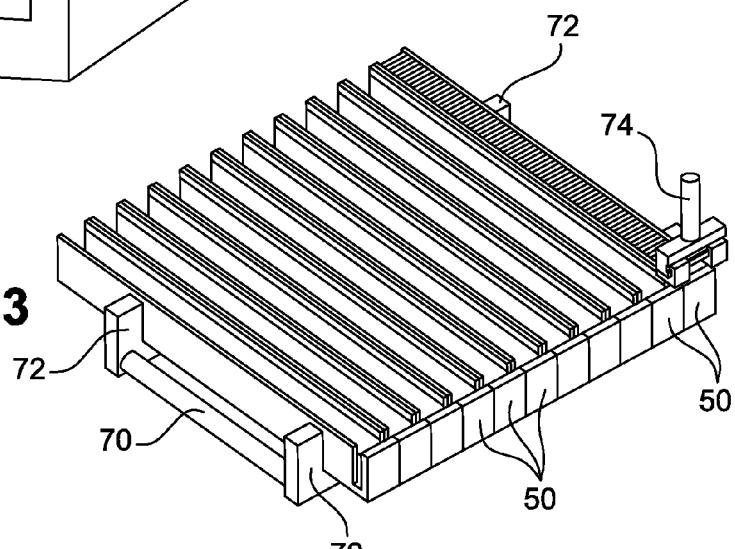
FIG. 13 is a diagrammatic perspective view of a horizontal charger having drawers of the type shown in FIG. 12.
Figure 14:
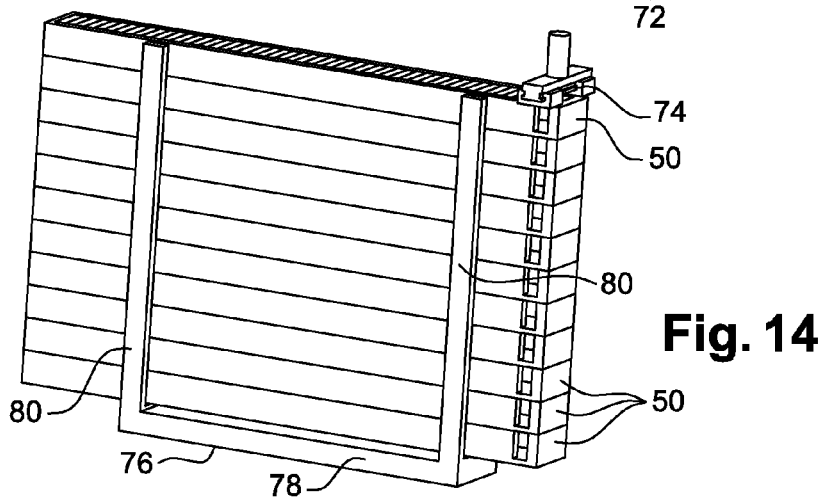
FIG. 14 is a diagrammatic perspective view of a vertical charger having drawers of the type shown in FIG. 12.

Drawers 50 carrying reaction vessels can be placed in a horizontal charger such as that shown in FIG. 13, or in a vertical charger such as that shown in FIG. 14.

The charger of FIG. 13 has a horizontal frame 70 with rims 72 for retaining the drawers 50 that are placed side by side on the frame.

Reference 74 designates a device that may be used in the analysis appliance for pushing the reaction vessels housed in a drawer 50 and for causing them to leave the drawer.

The vertical charger 76 of FIG. 14 has a bottom wall 78 on which it is possible to place a stack of vertically superposed drawers 50, which drawers are retained on the bottom wall 78 by vertical uprights 80 carried by the bottom wall.

The same device 74 as in FIG. 13 can be used to extract the reaction vessels from the top drawer 50.

FIGS. 15 and 16 are diagrams showing a device for gripping a vessel in an automatic analysis appliance, which device may be used with the reaction vessels once fitted with the above-described connection parts.

The gripper device comprises a cylindrical vertical rod 82 having a bottom end carrying a horizontal bar 84 with two attachment fingers 86 guided to move thereon in horizontal translation towards each other and away from each other. The bottom ends of the fingers 86 carry connection nibs 88 for engaging the short sides of the frame 24 of a connection part mounted on a vessel 10.

This gripper device operates as follows:

As shown in FIG. 16a, the device is brought over a reaction vessel 10, the two fingers 86 are moved towards each other with the two fingers 86 being close together on the transverse path 84 of the device. By lowering the rod 82 as shown in FIG. 16b, the attachment nibs 88 are brought into the inside of the vessel 10 level with the connection part 22, and then the two fingers 86 are moved away from each other so as to engage the nibs 88 against the short sides of the frame of the connection part 22. By moving the rod 82 upwards, it is then possible to extract the reaction vessel 10, e.g. from its housing in the analysis appliance, and then to move it towards another location.

In FIGS. 16a and 16b, there can be seen the bead 46 of ferromagnetic material that is housed in the reaction vessel and guided on its curved bottom. There can also be seen the curved bottom ends of the jaws of the connection part that serve to prevent the bead from escaping from the reaction vessel while it is being manipulated.

FIG. 17 is a diagram showing a device for assembling reaction vessels and connection parts.

The device comprises a conveyor 92 connecting together various stations for loading reaction vessels and connection parts and that enables sets of vessels to be moved from one end to the other of the device in the direction represented by the arrow.

More precisely, the device comprises a station 94 in which vessels contained in a storage unit 96 can be placed and positioned on appropriate supports 98 carried by the conveyor 92.

By way of example, the supports 98 have vessel housings arranged in parallel rows, so that the vessels placed in these housings occupy positions corresponding to the positions they are to occupy in a string of vessels as shown in FIG. 5.

The following station 100 is a station for depositing ferromagnetic beads in the vessels carried by the support 98.

The following station 102 is a station for placing the connection parts on the reaction vessels and for clipping the connection parts to one another so as to form strings of reaction vessels.

The next station 104 is a monitoring station having a video camera in order to verify that ferromagnetic beads are present in the vessels and that the connection parts are properly clipped onto the reaction vessels and that the connection parts are properly clipped to one another.

The device also has at its inlet a station 106 for placing empty supports 98 on the conveyor 92, and at its outlet a station 108 for picking up supports 98 loaded with strings of reaction vessels.

The invention claimed is:

1. A reaction vessel for an automatic chemical or biological analysis appliance, the vessel having an open top end and containing fluid stirring means,
   wherein the top end of the vessel carries a connection part for attaching to an identical connection part of another vessel of the same type, the connection part being fastened on the top end of the vessel by resilient snap- or clip-fastening,
   wherein the connection part includes retaining means for retaining the fluid stirring means, the retaining means extending inside the vessel,
   wherein the fluid stirring means are a bead of ferromagnetic material,
   wherein the retaining means are formed on the connection part and comprise at least one jaw or thin plate extending downwards inside the vessel along a longitudinal wall thereof, each of the at least one jaw or thin-plate including a bottom edge forming an edge for guiding and retaining the bead of ferromagnetic material, and wherein,
   the vessel has a bottom portion located below the open top end,
   the at least one jaw or thin plate of the retaining means comprises two spaced-apart plates,
   each of the two spaced-apart plates has a top portion connected to the connection part and extending vertically downwards inside the vessel along the longitudinal wall thereof,
   the bottom edge of each of the spaced-apart plates that forms the edge for guiding and retaining the bead of ferromagnetic material is curved in a longitudinal plane and in a transverse plane, and
   the bottom edge of the spaced-apart plates are spaced apart from each other by a distance less than a diameter of the bead of ferromagnetic material.

2. A reaction vessel for an automatic chemical or biological analysis appliance, the vessel having an open top end and containing fluid stirring means,
   wherein the top end of the vessel carries a connection part for attaching to an identical connection part of another vessel of the same type, the connection part being fastened on the top end of the vessel by resilient snap- or clip-fastening,
   wherein the connection part includes retaining means for retaining the fluid stirring means, the retaining means extending inside the vessel,
   wherein the fluid stirring means are a bead of ferromagnetic material, and
   wherein the retaining means are formed on the connection part and comprise at least one jaw or thin plate extending downwards inside the vessel along a longitudinal wall thereof, each of the at least one jaw or thin-plate including a bottom edge forming an edge for guiding and retaining the bead of ferromagnetic material, and wherein, the vessel has a bottom portion located below the open top end, the vessel being a rectangular parallelepiped with the open top end, lateral short sides, and lateral long sides, the at least one jaw or thin plate of the retaining means comprises two spaced-apart plates, each of the two spaced-apart plates has a top portion connected to the connection part and extending along a respective one of the lateral long sides and vertically downwards inside the vessel along the longitudinal wall thereof, and the bottom edge of the spaced-apart plates are spaced apart from each other by a distance less than a diameter of the bead of ferromagnetic material.

3. The vessel according to claim 2, wherein, the two spaced-apart plates are two spaced-apart parallel plates, the bottom portion of the vessel is curved with concave sides that face upwards, and the bottom edge of each of the spaced-apart parallel plates that forms the edge for guiding and retaining the bead of ferromagnetic material is curved in a longitudinal plane and in a transverse plane so as to correspond to a curvature of the bottom portion of the vessel.

* * * * *